(12) United States Patent
Meyer et al.

(10) Patent No.: US 9,603,578 B2
(45) Date of Patent: Mar. 28, 2017

(54) METHOD AND APPARATUS FOR GRAPHICAL ASSISTANCE IN A MEDICAL PROCEDURE

(71) Applicant: Siemens Aktiengesellschaft, Munich (DE)

(72) Inventors: Andreas Meyer, Bubenreuth (DE); Norbert Rahn, Forchheim (DE); Markus Rossmeier, Bamberg (DE)

(73) Assignee: Siemens Aktiengesellschaft, Munich (DE)

( * ) Notice: Subject to any disclaimer, the term of this patent is extended or adjusted under 35 U.S.C. 154(b) by 324 days.

(21) Appl. No.: 14/305,212

(22) Filed: Jun. 16, 2014

(65) Prior Publication Data
US 2014/0369465 A1    Dec. 18, 2014

(30) Foreign Application Priority Data
Jun. 17, 2013    (DE) .................. 10 2013 211 239

(51) Int. Cl.
*A61B 6/03* (2006.01)
*A61B 6/00* (2006.01)
*A61B 90/00* (2016.01)

(52) U.S. Cl.
CPC .............. *A61B 6/487* (2013.01); *A61B 6/032* (2013.01); *A61B 6/463* (2013.01); *A61B 6/488* (2013.01);
(Continued)

(58) Field of Classification Search
CPC .............. A61B 6/487; A61B 2090/364; A61B 2090/376; A61B 6/032; A61B 6/463; A61B 6/488; A61B 6/503; A61B 90/37
See application file for complete search history.

(56) References Cited

U.S. PATENT DOCUMENTS

2008/0137924 A1* 6/2008 Boese .................. G06T 11/008
                                              382/128
2010/0061611 A1    3/2010 Xu et al.
(Continued)

OTHER PUBLICATIONS

"Predicting Successful Guidewire Crossing Through Chronic Total Occlusion of Native Coronary Lesions Within 30 Minutes: The J-CTO (Multicenter CTO Registry in Japan) Score as a Difficulty Grading and Time Assessment Tool," Morino et al., JACC: Cardiovascular Interventions, vol. 4, No. 2 (2011), pp. 213-221.

*Primary Examiner* — Glen Kao
(74) *Attorney, Agent, or Firm* — Schiff Hardin LLP (57) ABSTRACT

In a method and apparatus for graphical assistance in an interventional procedure to open an occlusion of a hollow organ of a patient a three-dimensional CT image data set of an examination region with the at least one hollow organ having the occlusion is retrieved and visualized segmentation data with segmentation data of the hollow organ at a display unit. At least two x-ray fluoroscopy images are acquired at different angulations the CT image data set is registered with at least two of the x-ray images. A number of fluoroscopy x-ray images are acquired during a time period, with real-time visualization of at least one x-ray fluoroscopy image and data of the CT image data set at the display unit. The steps are implemented individually and in sequence, and control options relating exclusively to the current step can be selected manually via a user interface depending on the step that is currently implemented, and only user inputs that are appropriate for the current step are accepted.

20 Claims, 5 Drawing Sheets

(52) U.S. Cl.
CPC .............. *A61B 6/503* (2013.01); *A61B 90/37* (2016.02); *A61B 2090/364* (2016.02); *A61B 2090/376* (2016.02)

(56) References Cited

U.S. PATENT DOCUMENTS

| | | |
|---|---|---|
| 2012/0063663 A1 | 3/2012 | Kawasaki |
| 2012/0230565 A1 | 9/2012 | Steinberg et al. |
| 2013/0004037 A1 | 1/2013 | Scheuering |
| 2014/0204124 A1 | 7/2014 | Auvray et al. |

* cited by examiner

METHOD AND APPARATUS FOR GRAPHICAL ASSISTANCE IN A MEDICAL PROCEDURE

BACKGROUND OF THE INVENTION

Field of the Invention

The present invention concerns a method for graphical assistance in an interventional medical procedure to open an occlusion of a hollow organ of a patient, as well as an apparatus to implement such a method.

Description of the Prior Art

A coronary heart condition in which one of the coronary arteries is completely occluded and should be opened again with a catheter within the scope of an interventional procedure is designated as a CTO (Chronic Total Occlusion). Approximately 8-10% of all coronary interventions today are CTO cases. The intervention to open the occlusion can only be implemented by experienced cardiologists. A problem in such a procedure is that, due to the total occlusion, the distal portion of the coronary artery cannot be depicted via a typical contrast agent injection in the appertaining artery, for example with the use of C-arm x-ray angiography. The cardiologist must thus effectively open the occlusion "blind", which creates risk of vessel perforation as well as other risks.

In contrast to C-arm x-ray angiography, both the vessel occlusion (including the calcium deposit) and the proximal and distal portion of the appertaining coronary artery can be shown in a computed tomography (CT) image. However, computed tomography data (image) acquisitions cannot be implemented in real time during an interventional procedure.

SUMMARY OF THE INVENTION

An object of the present invention is to provide a method for graphical assistance in a medical interventional procedure, which can be implemented as simply as possible and requires as few user interactions as possible. Furthermore, it is the object of the invention to provide an x-ray apparatus that is suitable for the implementation of the method.

This object is achieved by a semi-automatic or automatic method in accordance with the invention, for graphical assistance in an interventional procedure to open an occlusion of a hollow organ of a patient, which has the following steps:

1. retrieve a three-dimensional CT image data set of an examination region with the at least one hollow organ having the occlusion, determine or retrieve segmentation data of the CT image data set, and visualize the three-dimensional CT image data set with shown segmentation data of the hollow organ at a display unit, 2. acquire at least two x-ray images at different angulations by means of a fluoroscopy image acquisition system, and register the CT image data set with at least two of the x-ray images, 3. continuously acquire a plurality of x-ray images with the fluoroscopy image acquisition system during a determinable time period, and joint real time visualization of data of the CT image data set and at least one respective x-ray image at the display unit, and 4. store information of the method after the end of the acquisitions, and wherein the steps are implemented individually and in this sequence and depending on the step which is implemented as a current step control operations relating exclusively to the current step can be selected manually via an operator interface, and only user inputs that are appropriate for the current step are accepted.

The method according to the invention can be implemented at least semi-automatically, and thus particularly simply. The individual steps proceed automatically, step by step, and allow the user to select control options (for example to modify the visualizations) via a dynamic adaptation of the user interface, but only those control options that are also reasonable and helpful for the current step. After conclusion of the current step, the control options of the concluded step are no longer available to the user. The method assists the user in the implementation of an interventional procedure to open an occlusion of a hollow organ such that the user does not need to intervene (or must only intervene slightly) in the graphical assistance with he or she being intuitively guided, while still receiving an optimal visualization of the occlusion. The user thus can optimally concentrate on the interventional procedure, which leads to particularly good and safe care of the patient.

For step 1, a processor that executes the method accesses three-dimensional CT image data sets of the hollow organ with the occlusion that have already been acquired. The segmentation data may also have been determined previously, or can be determined within the scope of the method.

The three-dimensional CT image data set is preferably displayed as a 3D image at a monitor in communication with the processor, or one or more two-dimensional projection images determined/calculated from the CT image data set are displayed.

A device to implement the method according to the invention has a control unit to control the method; an image processing unit to process image data; a fluoroscopy image acquisition system to acquire x-ray images (thus fluoroscopic x-ray images); a display unit to display the visualizations and the user interface; and an input unit to receive user inputs. The control unit and the image processing unit can thereby be formed by a PC or a winding support with a suitable software, for example, which is integrated into the fluoroscopy image acquisition system. For example, the image acquisition unit can be formed by a keyboard, a mouse or a touchscreen. For example, the fluoroscopy can be formed by an angiography x-ray apparatus with an adjustable C-arm or with two C-arms arranged in different planes (biplanar). It can be provided that the control and image acquisition processing unit are arranged in a space (monitoring space) that is different from the examination space (in which the patient and the fluoroscopy image acquisition system are arranged. Multiple display units can also be provided, for example one in the examination space and one in the monitoring space, wherein identical or different visualizations are possible at multiple display units.

According to one embodiment of the invention, an additional step 1a is implemented between step 1 and 2: 1a) determine at least one parameter of the occlusion of the hollow organ (in particular its length and/or its diameter) from the three-dimensional CT image data set (or, respectively, the segmentation data determined from this). Such parameters can supply additional information about the occlusion, and thereby contribute to a simpler and more secure implementation of the interventional procedure.

According to a further embodiment of the invention, in step 1a determination or a retrieval of a middle axis (center line) and/or a three-dimensional extent (lumen) of the hollow organ at the CT image data set is implemented as a determination or retrieval of segmentation data of the CT image data set, and a correctly positioned visualization of the three-dimensional CT image data set is implemented with shown center line and/or three-dimensional lumen of the hollow organ. The determination of the center line and/or of the three-dimensional lumen of the hollow organ and its correctly positioned visualization in the 3D presentation of the CT image data set ensure important information for a user for implementation of an interventional procedure.

The presentation of the CT image data set and/or other visualizations can be rotated and modified in terms of their orientations for a particularly high-detail, informative and easily recognizable display. For example, in step 1 the CT image data set can be displayed as a 3D image that can be rotated in all directions. In this context, a control option (a clickable button, for example) can be provided adapted to the respective step, by means of which the user can make inputs to rotate the respective visualization.

The center line and/or the three-dimensional lumen are advantageously highlighted in color or displayed with color coding. For example, the center line can be indicated by being mixed into a greyscale 3D image of the CT image data set, by color coding. The center line and/or the three-dimensional lumen also can be displayed individually and be marked in color.

According to a further embodiment of the invention, in step 1 the chronologically most current segmentation data are automatically used given the presence of multiple segmentation data. Alternatively or additionally, the user interface can include a control option to select from multiple segmentation data sets so that the user can select segmentation data. Within the scope of the method, the input of the user is received and the selected segmentation data are used in the further course of the method.

According to a further embodiment of the invention, projection images and/or MPR images (multiplanar reconstruction) are determined from the CT image data set, relative to a selectable point of the center line, and are displayed. For example, a point on the center line can be selected automatically or be entered manually by a user within the scope of a control option. Projection images or MPR images are determined relative to this point, for example a "Curved MPR" along the center line and an MPR orthogonal to the center line to depict the lumen. For example, within the scope of steps 2 and 3 projection images can also be determined/calculated from the CT image data set, the projection directions of which projection images correspond to those of the x-ray images of the fluoroscopy acquisition system in the current angulation.

According to a further embodiment of the invention, in step 1a) a J-CTO score is determined as a further parameter. For example, the J-CTO score is known from the article "Predicting successful guide wire" crossing through chronic total occlusion of native coronary lesions within 30 minutes: the J-CTO score as a difficulty trading and time assessment tool," Morino et al., JACC Cardiovascular Interventions (2011), Vol. 4, Issue 2, pp. 213-221. Via the J-CTO score, a user can receive information regarding the degree of difficulty of the procedure to open the occlusion.

In step 2, the at least two x-ray images are advantageously acquired during a contrast agent perfusion through the hollow organ. Via the contrast agent perfusion, the visibility and the contrast of the hollow organs in the x-ray image are improved, which ensures a good registration due to a good ability to recognize the structures.

According to a further embodiment of the invention, in step 2 at least three x-ray images are acquired, and at least two x-ray images are selected automatically for the registration, or an input is received to select at least two x-ray images for the registration. For example, the automatic selection can take place according to criteria such as the presence of a defined image contrast and at the same time differing angulations (projection direction) of the fluoroscopy image acquisition system.

Alternatively or additionally, a selection of additional x-ray images can be offered the user as a control option by means of the user interface. Upon receiving a user input with regard to one or both x-ray images, these are used for the registration.

In step 2, after registration is implemented a common, accurately positioned visualization of x-ray images and center line and/or three-dimensional lumen of the hollow organ is advantageously displayed. In this way the result of the registration is visible to the user.

In step 3, the time period appropriately corresponds to the duration of the interventional procedure. For example, this time period can also be hard-set or may be input manually. An automatic detection can also be present, and the time period can be ended if (for example) an interventional instrument is no longer detected in the x-ray images.

According to further embodiments of the invention, for a particularly good recognition capability, the visualizations are displayed at least partially in color or color-coded in one or more display windows (for example 2 through 5) of the display unit. For example, 3D images and x-ray images of the fluoroscopy image acquisition system (2D) can be displayed next to one another or in an overlay; the center line of the hollow organ can additionally be overlaid or can likewise be displayed in color in an additional display window. The user interface can likewise be displayed in a separation display window.

According to a further embodiment of the invention, in step 3 the real-time visualization takes place in correctly positioned (relative to the CT image data set and/or the center line and/or the three-dimensional lumen of the hollow organ and/or the MPR images etc.) superimposed/overlaid presentation or presentation arranged next to one another.

According to a further embodiment of the invention, user inputs for modification of the optical presentation—in particular with regard to presentation size, arrangement, orientation, superposition, number of display windows and coloration—of the visualization belonging to the step can be received and are varied accordingly upon receiving the visualizations. For this purpose, the user interface has input fields (for example to be clicked on or as a scroll-down menu) depending on the respective step, for example, such that the user may make a selection as necessary. The user input is then received, and the visualization is adapted corresponding to the selection.

According to a further embodiment of the invention, in step 4 the determined data and/or acquired x-ray images and/or processed CT image data sets and/or visualizations by means of the DICOM standard are stored in a memory unit (in particular an archive).

DESCRIPTION OF THE PREFERRED EMBODIMENTS

Figure 1:
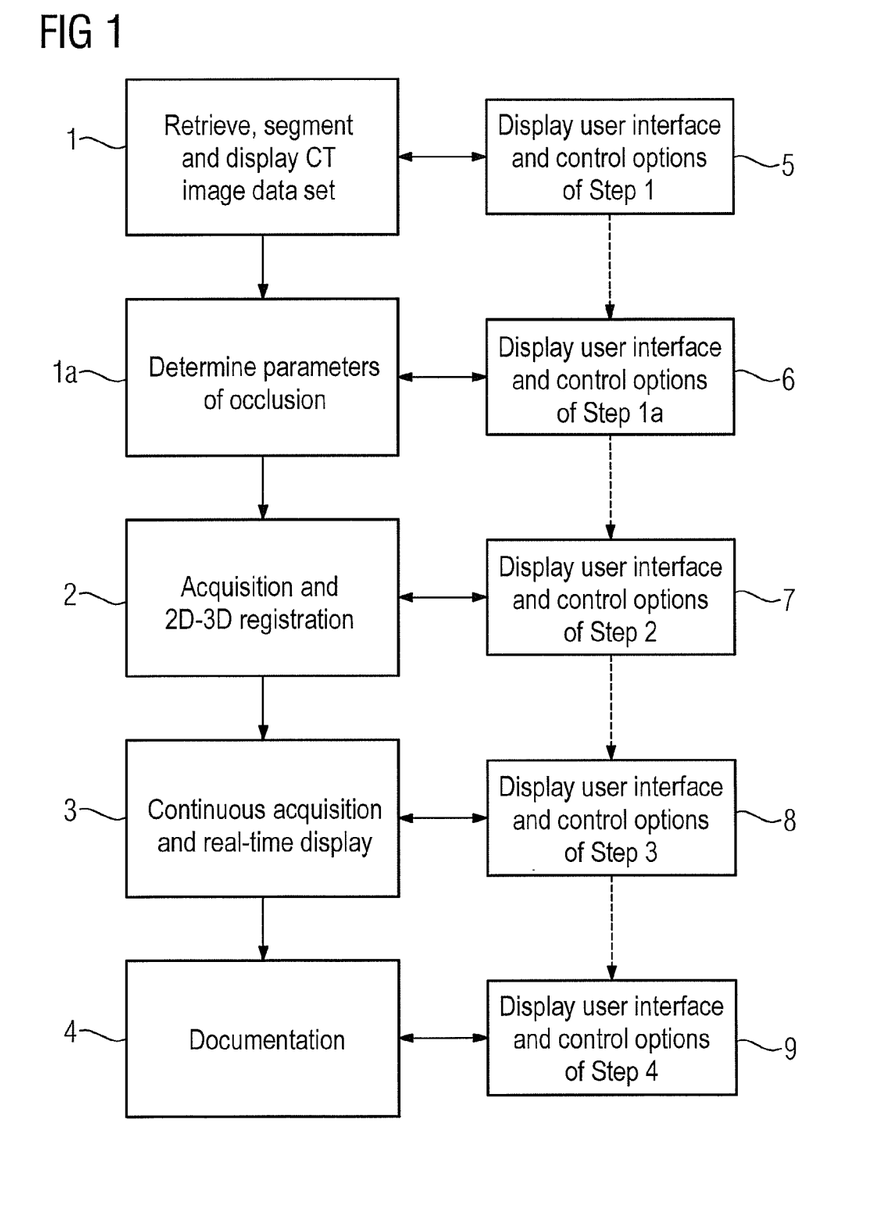
FIG. 1 shows the sequence of the method according to the invention.

A sequence of steps 1 through 4 of the method according to the invention is shown in FIG. 1. The method for graphical assistance during an interventional procedure to open an occlusion of a hollow organ (for example coronary arteries) thereby intuitively assists a user so that said user does not need to implement any user interactions, or only a few; can completely concentrate on the interventional procedure; and nevertheless receives a display of all required visualizations. Errors are precluded via the automatic step-by-step workflow and the user interface dynamically adapted to the respective steps, and an optimal presentation of the necessary visualizations is ensured.

A device to implement the method according to the invention has a control unit to control the method; an image processing unit to process image data; a fluoroscopy image acquisition system to acquire x-ray images (thus fluoroscopic x-ray images); a display unit to display visualizations and the user interface; and an input unit to receive user inputs. The control unit and the image processing unit can thereby be formed by a PC or a workstation with a suitable software, for example, which PC or workstation is integrated into the fluoroscopy image acquisition system in the form of a C-arm x-ray apparatus, for example. The input unit can be formed by a keyboard, a mouse or a touchscreen, for example.

In a first step 1, a CT image data set of the examination region with the at least one cavity with occlusion is initially retrieved; segmentation data of the CT image data set are retrieved or determined; and a visualization of at least one 3D image determined from the three-dimensional CT image data set, with correctly positioned segmentation data of the hollow organ shown, is displayed at a display unit. A middle axis (center line) and/or a three-dimensional extent (lumen; for example in the form of a voxel tube along the center line) of the hollow organ(s) are retrieved or are determined from the CT image data set as segmentation data. One or more of the 3D images or (2D) projection images that are created from the CT image data set are displayed at the display unit, wherein the center line and/or the three-dimensional extent (lumen) of the hollow organ are shown correctly positioned in the or 3D image or images. A user interface 5 adapted to step 1, with one or more control options for selection, is additionally display to a user. The user can implement manual inputs by means of the user interface, which inputs are received and realized accordingly. For example, inputs can be made to modify the optical presentation of the visualization; for example, a 3D image can be rotated or sections can be enlarged, for example. A "correctly positioned overlay" means that the center line (for example) in the 3D image or the projection image corresponds to the three-dimensional image of the hollow organ or to the image of the hollow organ projected in the plane.

Additional options and details with regard to step 1:

The segmentation or determination of centerline and/or three-dimensional lumen of the hollow organ can have already been implemented beforehand at an arbitrary point in time after the acquisition of the CT image data set and be implemented by means of an arbitrary image processing unit. The CT image data sets and segmentation data can be stored in the DICOM format in an archive, for example, and can be retrieved from the archive via a data connection at the start of the method according to the invention. They can also already be present in a memory unit in the device implementing the method according to the invention and be retrieved there. The segmentation data can also be determined/calculated by the image processing unit of the device according to the invention at the start of the method, after retrieving the CT image data set, for example.

If the segmentation data are retrieved and more than one data set is present, it can thus be provided that the chronologically most current data are used automatically. The adapted user interface can have a control option in which the user can implement and input to change the selection of the segmentation data. The input is received and the data set selected by the user is used in the following. A control option to re-implement a segmentation on the basis of the CT image data set can also be provided.

Within the scope of the visualization, for example, a 3D image from the CT image data set can be displayed in which the center line of the hollow organ and the three-dimensional lumen of the hollow organ are shown. Multiple display windows can also be arranged next to one another. The center line indicates the course of the hollow organ before, after and including the occlusion. The center line can be displayed in color (in what is known as color coding) in order to clarify perspective abbreviations. The three-dimensional lumen can be displayed around the center line in the form of a voxel tube. If necessary, parts of the center line or of the three-dimensional lumen can be masked in and out via a user input. Calcium deposits that are responsible for the occlusion of the hollow organ can be identified in the voxel tube. If necessary, the center line and/or the three-dimensional extent can be rotated via a user input, wherein the color coding can change to match, for example.

In this first step, it can also already be provided to display the orientation of the visualizations of the CT image data according to the current angulation of the fluoroscopy x-ray system (for example C-arm angulation given the presence of a C-arm x-ray apparatus) or, respectively, to optionally move said orientation continuously as well with angulation of the x-ray system. Moreover, the fluoroscopy x-ray system (the C-arm, for example) can thus be aligned as the visualizations of the CT image data set are aligned. If the fluoroscopy x-ray system is formed by a biplanar C-arm x-ray apparatus, this can be implemented for both planes of the biplanar C-arm x-ray apparatus. The CT image data set is then accordingly visualized for each of the two planes and rotated corresponding to the angulation of the planes.

After the conclusion of step 1, the next step (for example the second step 1a) is activated automatically. The user interface for the second step is likewise displayed/operable.

In a second step 1a), at least one parameter of the occlusion of the hollow organ—in particular the length and/or the diameter of the occlusion—is determined from the three-dimensional CT image data set. A user interface 6 adapted to step 1a), with one or more control options for selection, is additionally displayed to a user. The second step is optional and can also be skipped.

Additional options and details regarding second step 1a):

A three-dimensional length measurement of the occlusion on the center line or on the three-dimensional lumen (voxel tube) around the center line can be implemented automatically or via a user input. Alternatively or additionally, further parameters—for example the "J-CTO Score", which supplies a statement regarding the degree of difficulty with regard to opening the occlusion—can be determined, either automatically or as a control option which the user can select.

A visualization can automatically display one or more MPR images (multiplanar reconstruction) from the CT image data set for a point on the center line, for example. For example, two MPR images, a "Curved MPR" along the center line and an MPR image orthogonal to the center line (depiction of the lumen) can be displayed. A control option can also be present at the user interface 6 for selection of the point for which the MPR images are displayed. For example, a user can select the point by means of a cursor at the display unit, the input is received, and the corresponding MPR images are displayed. After conclusion of the second step 1a), the next step (for example the third step 2) is activated automatically. The user interface for the third step is likewise displayed/operable.

In a third step 2, the acquisition of at least two x-ray images is implemented by means of a fluoroscopy image acquisition system at different angulations, and the registration of the CT image data set is implemented with at least two of the x-ray images. The at least two x-ray images are thereby preferably acquired during a contrast agent perfusion through the hollow organ of the patient. Three (or a plurality of) x-ray images (a scene, for example) can also be acquired, wherein two or more of the x-ray images differ in the angulation in which the fluoroscopy image acquisition system is set at the point in time of the acquisition. Given use of a C-arm, the angulation is, for example, the projection direction relative to the examination subject. For example, the C-arm of a C-arm apparatus can be rotated around the hollow organ during the acquisition of the scene. The registration is preferably a 2D-3D registration; various methods for implementation of such a registration are known from the prior art. A user interface 7 adapted to step 2 is additionally displayed to a user with one or more control options for selection.

Additional options and details with regard to third step 2:

The registration serves to visualize, with correct positioning, an optimally precise combination of fluoroscopic x-ray images acquired in real time with images (3D images and projection images) obtained from the CT image data set.

For example, a user can make an input with regard to the point in time of the start of acquisition of the x-ray images. An administration of contrast agent and/or a breath-hold phase can thereby be coordinated with the acquisition of the x-ray images. Acquisitions also can be implemented under consideration of an EKG or breathing phases of the patient, for example in order to adjust the x-ray images with the corresponding EKG or breathing phase in which the CT image data set that is used was acquired. Given use of a C-arm x-ray apparatus, for example, it can be reasonable to implement acquisitions during a rotation of the C-arm by 30° or more around the hollow organ.

The two x-ray images that are necessary for the 2D-3D registration are, for example, selected automatically by the device, for example using criteria such as a defined image contrast or the required different angulations. Additionally or alternatively, a control option can also be provided to select the two x-ray images for the registration. The 2D-3D registration is subsequently stored. Additional control options can also be provided to revise or correct the registration. A manual correction and storage of the registration can be possible from now on in all further steps.

Given use of a biplanar C-arm x-ray apparatus, the two x-ray images that are required for the registration can also be acquired with a single (optionally EKG-triggered) 2-plane acquisition of the contrasted hollow organ.

After the 2D-3D registration, for example, the determined center line can be visualized at the display unit in perspective with correct positioning together with acquired x-ray images, corresponding to the angulation and projection geometry (of the C-arm, for example). The user interface can also receive an interactive manual displacement of the center line by the user, for example, in order to implement a manual registration correction. In the case of a biplanar C-arm x-ray apparatus, this manual correction can take place successively or in alternation in both planes.

Figure 2:
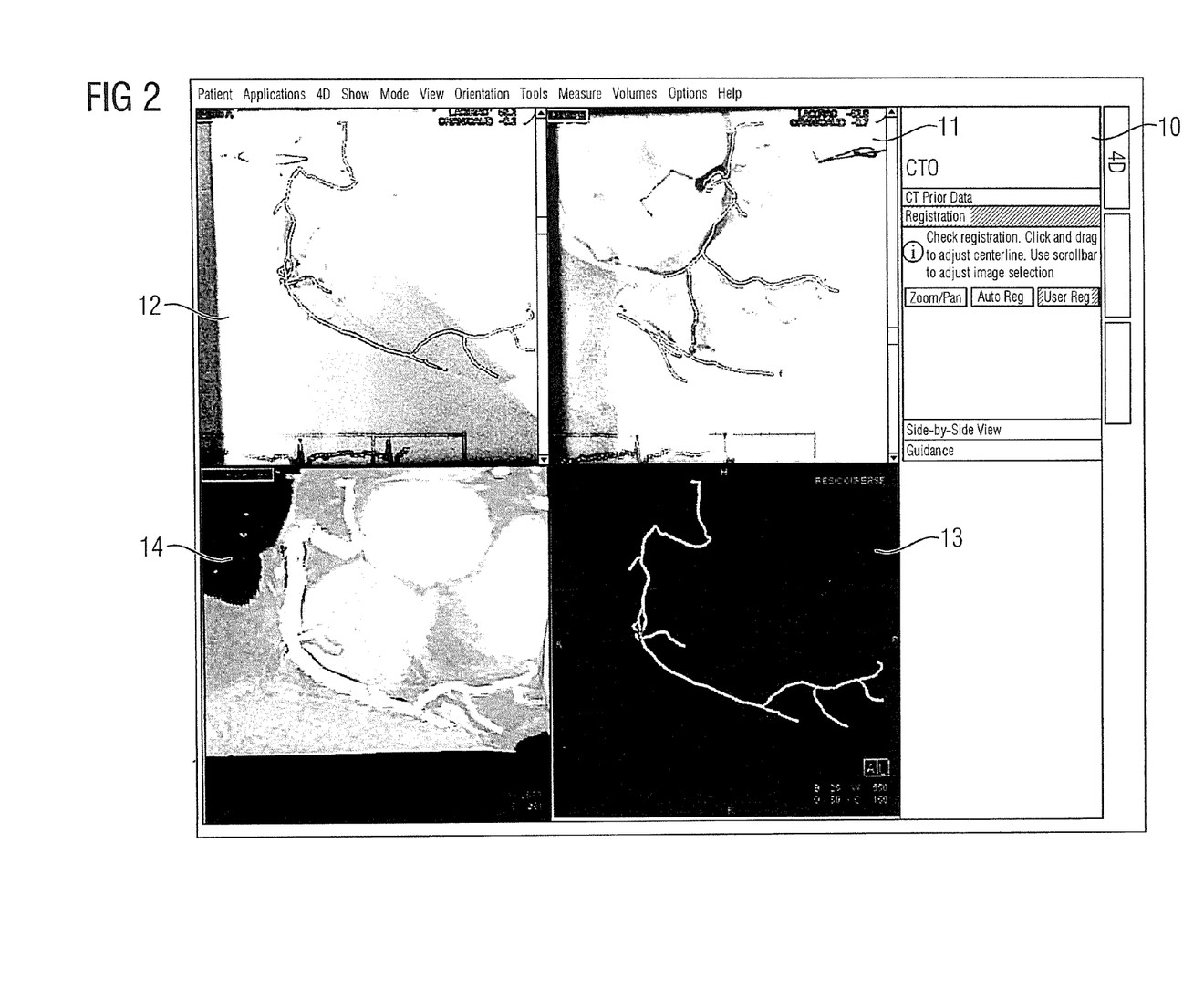
FIGS. 2 through 5 are respective screenshots of visualizations and user interfaces with control options for a user at various points in time during the method according to the invention.

A possible visualization with user interface with control options for the third step is shown in FIG. 2. The registration is marked on the right side in a first display window 10 in order to indicate the presently active step, and multiple active control options (zoom, automatic, manual registration) can be selected by a user. Four display windows with visualizations of x-ray images, 3D images and the center line 15 are shown in the middle and to the left at the display unit. The center line (15), together with x-ray images for two planes of a biplanar C-arm x-ray apparatus, is visible in the second and third display window 11, 12. The registration itself is implemented directly, or takes place directly. The fifth display window 14 shows the three-dimensional lumen of the hollow organ which is projected in an image plane (as an example, a coronary artery together with the myocardium), wherein the orientation of the visualization of the visualization of the current angulation corresponds to a first plane of the biplanar C-arm x-ray apparatus. The fourth display window 13 shows the color-coded center line that—after the registration with regard to orientation and perspective rendering—again corresponds to the current angulation and geometry of the first plane.

Figure 3:
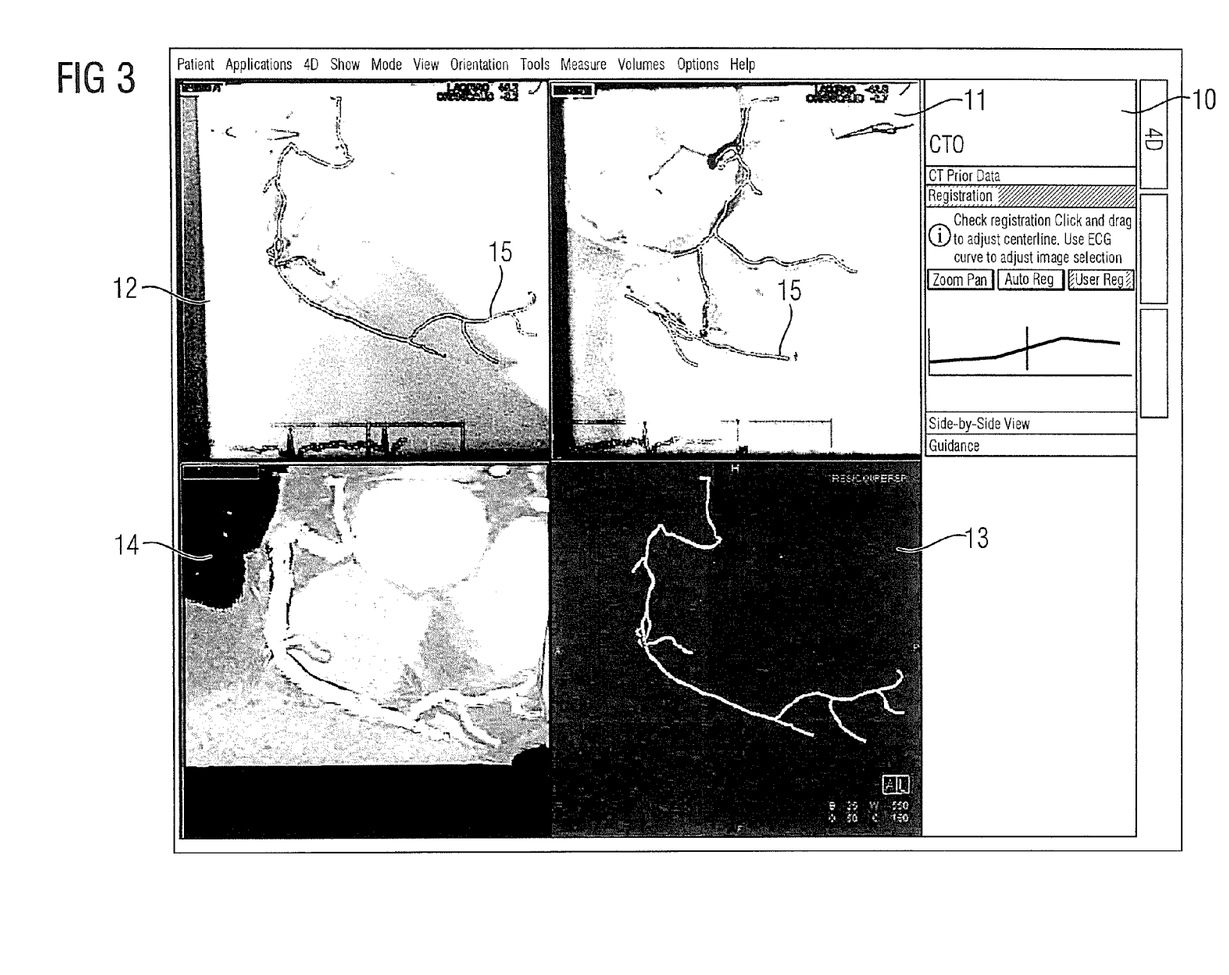

An interactive slider bar that can be displaced in the EKG curve is shown in the first display window in FIG. 3, which enables the control option to select x-ray images of a defined EKG phase to be selected for the registration or allows the acquired x-ray images to be paged through in order to make a selection for the 2D-3D registration.

After conclusion of the third step 2), the next step (for example the fourth step 3) is activated automatically. The user interface for the fourth step is likewise displayed/operable.

In a fourth step 3, a number of x-ray images (in the form of a scene, for example) are acquired continuously with the fluoroscopy image acquisition system during a determinable time period, and a common real time visualization of at least one individual x-ray image and data of the CT image data set takes place at the display unit. The time period in particular corresponds to the duration of an interventional procedure to open the occlusion. In this way, and via the real time visualization, it is possible for the user to track current image data about the current state of the procedure, and therefore to improve the safety of the procedure. A user interface 8 adapted to step 3 is additionally displayed to a user with one or more control options for selection.

Further options and details with regard to the fourth step 3:

For example, 3D images or projection images from the CT data sets—which are oriented and rendered in perspective corresponding to the current angulation and current geometry of the fluoroscopy image acquisition system (C-arm, for example)—can be displayed as MPR images in a display window, and the color-coded center line and/or the three-dimensional lumen of the hollow organ and the fluoroscopic real-time x-ray images are visualized in the same or additional display windows. An automatic layout switch can be implemented with regard to the display windows that are to be shown. Only one or two display windows can also be presented, and the center line can be mixed into the (real time) x-ray images, for example. The center line or parts of the center line can also be activated or deactivated at the display unit, for example. If the angulation of the fluoroscopy image acquisition system (and therefore the view of the fluoroscopic x-ray images) changes, the 3D image is also rotated automatically or the projection images from the CT data sets are also adapted, for example, and/or the center line is adapted in terms of its perspective, possibly with modification of the color coding.

In the case of a biplanar C-arm x-ray apparatus, two MPR images are respectively displayed with (for example) center line and three-dimensional lumen of the hollow organ (for example coronary artery and myocardium), whose contents with regard to angulation and perspective correspond to the angulations and projection geometries of the two planes of the biplanar C-arm x-ray apparatus. Alternatively, a superposition of the preoperative CT image data (advantageously of the color-coded center line) with the x-ray images of the fluoroscopy image acquisition system is also possible in a single display window. For example, those x-ray image that were acquired in the same EKG phase and breathing phase as the CT image data set are thereby then used for overlay. In another embodiment, the superimposed center line can be continuously deformed during the acquisition and real-time display of the fluoroscopic x-ray images so that—in spite of the vessel movement (due to heartbeat and breathing of the patient—an optimally precise superposition is created. A movement field (determined based on a model, for example) is applied to the center line for this deformation.

It is likewise possible to angulate one or two planes of the C-arm x-ray apparatus so that the angulation of the orientation corresponds to the CT image data set (also of the center line, for example).

Figure 4:
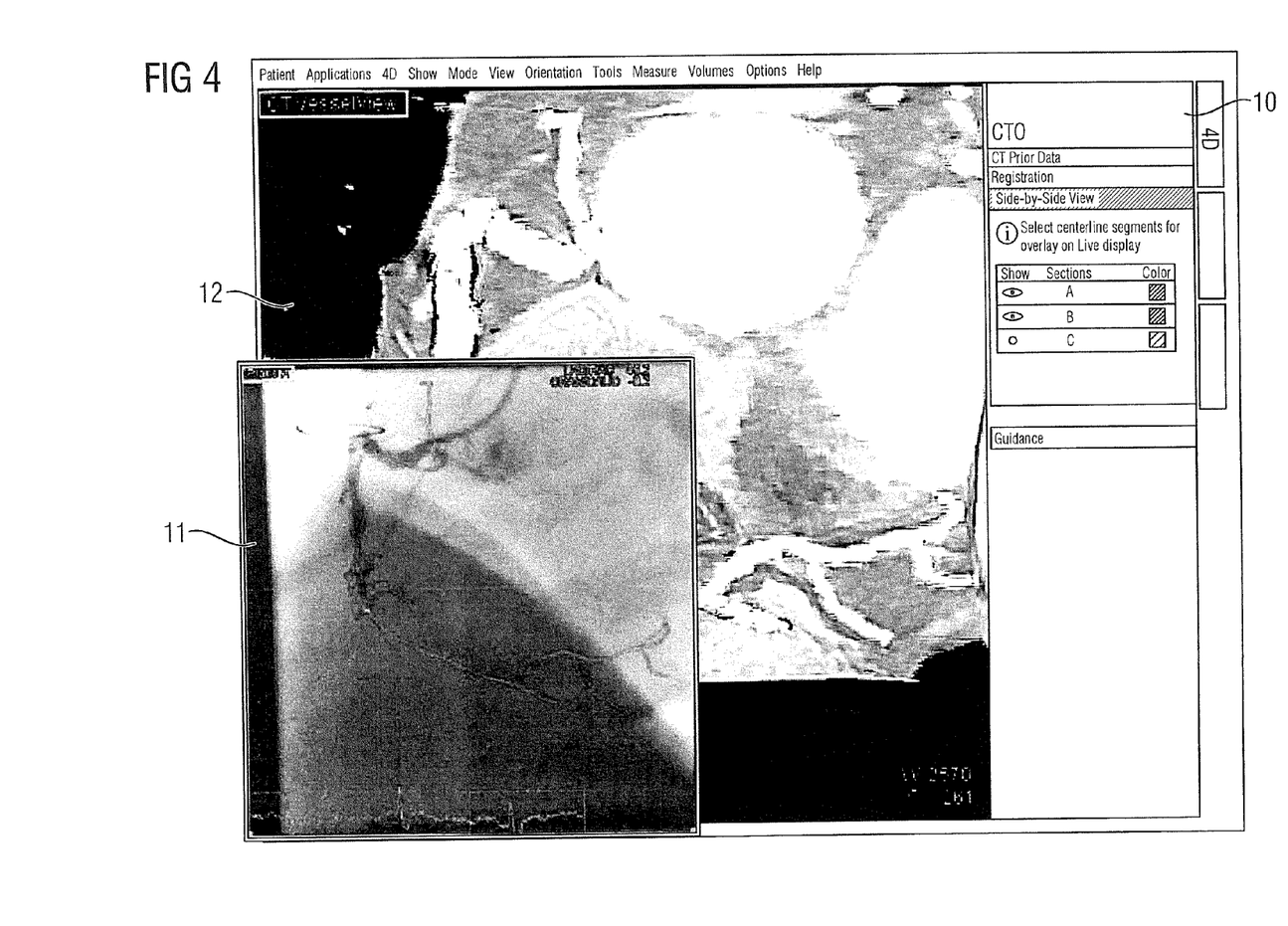

One possible visualization with user interface with control options for the fourth step is shown in FIG. 4. Three display windows are shown, wherein the first display window 10 shows the user interface with the active step (here: sub-step of the fourth step), wherein a control option (activation or deactivation of the color-coded center line) can be selected by a user. A second display window 11 shows a superposition of the center line on the currently acquired x-ray image. A third display window 12 which is partially covered by the second display window 11 shows a projection image from the CT image data set with the x-ray image of corresponding orientation, and the three-dimensional lumen of the hollow organ (voxel tube that indicates the lumen of the hollow organ to be treated therapeutically) that is likewise adapted in terms of its perspective.

Figure 5:
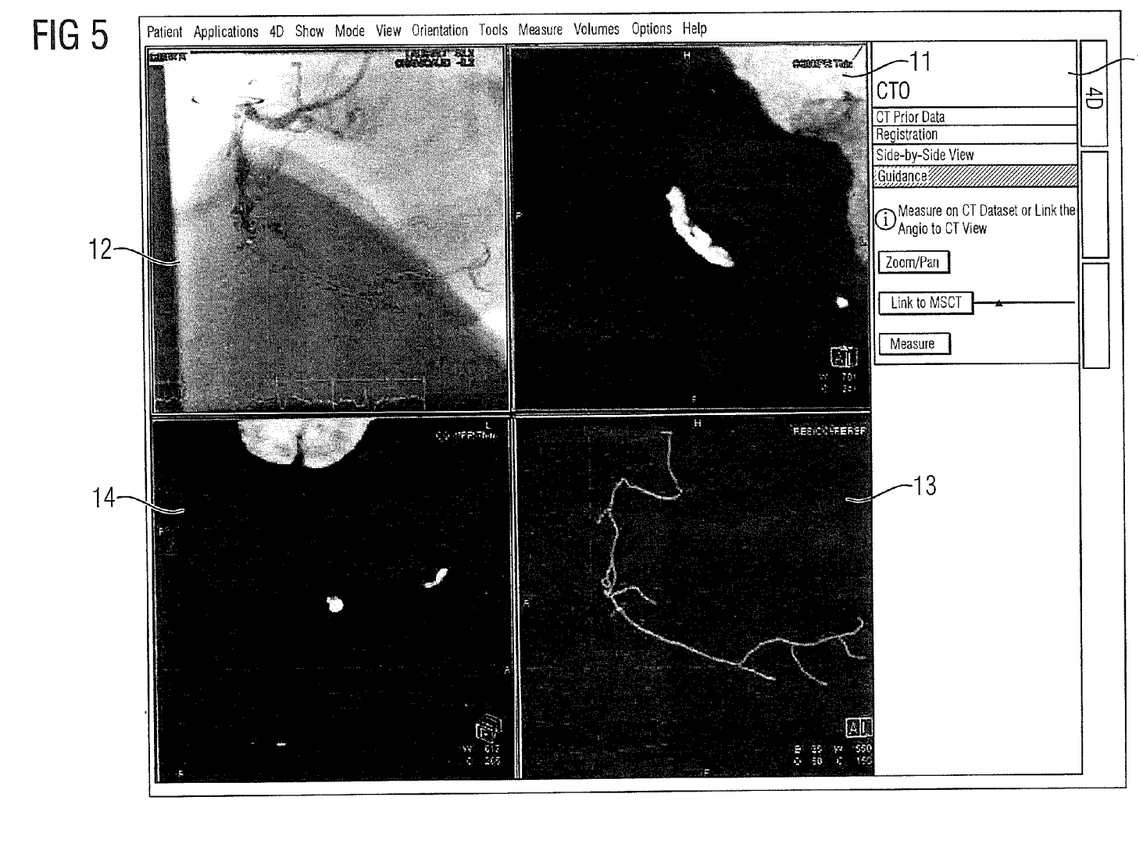

An additional possible visualization with user interface with control options for the fourth step is shown in FIG. 5. Five display windows are shown, wherein the first display window 10 shows the user interface with the active step (here: sub-step of the fourth step). Current control options of the user interface here are, for example: enlarge/shrink and displace images/image data in a selected display window; "Link to MSCT": the opacity of the overlay of different elements or images can be regulated; "Measure": distance and cross section measurements in display windows can be implemented (as in the second step 1a). The second display window 11 shows calcium depositions in a hollow organ (coronary artery) to be treated therapeutically; the third display window shows an overlay of color-coded center line with the current x-ray image; the fourth display window shows the color-coded center line; and the fifth display window shows an MPR image with background (aortic root) and sectioned portions of the contrasted hollow organ (coronary artery).

After conclusion of the fourth step 3 or after interactive termination (by the user), the next step (the fifth step 4, for example) is activated automatically. A user interface 8 for the fifth step 4 is likewise displayed/operable.

In a fifth step 4, some or all information acquired or determined in the course of the previous steps is stored after the end of the acquisitions. The information can be stored in a memory unit or an archive, for example. The information can be stored automatically, for example. Various control options can be displayed at the user interface, for example where and which information can be stored in which format, such that the user can manually intervene. For example, the post-processing results of the CT image data set (see steps 1 and 1a) can be sent to an archive via DICOM or be embedded in a report. Visualizations (for example side-by-side or overlay, 3D images, projection images, x-ray images etc.) can be sent to an archive or be embedded in a report via DICOM. Scenes (plurality of x-ray images) that were acquired before the intervention and scenes that were acquired after or during the intervention can be sent to an archive or be embedded in a report.

The method is then ended.

A backward jump between two steps can also be provided; for example, a switch can thus be made from the second step 1a) back to the first step 1, wherein then all control options of the first step 1 are possible again. The second step 1a is optional and can also be skipped. The actions of the steps—as well as the switching between steps—can be operable from different rooms (for example an examination room and a monitoring room) in that multiple control units and/or image processing units and input units are provided (for example a touchscreen arranged at a patient table or a menu controllable via joystick in the examination region and a workstation in the monitoring room).

Moreover, the following problem can also occur within the scope of minimally invasive procedures to open hollow organs (vessels):

The coronary vessels are difficult to see in an x-ray (radioscopy) image without injection of contrast agent, while the guide wire is easily detectable in an x-ray (radioscopy) image; although the regions before the occlusion are easily detectable with contrast agent, the occlusion itself is not. In order to obtain more information, preoperative CT data sets are used since the closed vessel segment is also sufficiently shown in this imaging modality due to the good low contrast resolution. In order to prepare CT data sets so that they optimally support the interventionalist in his work, there are the following two known approaches:

a) Based on a previously implemented registration of the CT data sets with the angiography system used for the radioscopy, for example, the (segmented) CT data are superimposed over the x-ray image that renders the current progress of the intervention in order to assist in the forward movement of the guide wire. The disadvantage of the prior art is that a static, preoperative data set is superimposed over a moving subject (for example the coronary at the heart). This superposition therefore is only correct for a very specific movement state of the heart.

b) The CT data are presented in synchronization with the C-arm of the angiography system without a registration of the data with the angiography system taking place beforehand. This is possible due to the fact [sic] because the patient is borne identically both in CT and in an angiography system ("Sync to C-arm" from the Siemens Healthcare). The CT data set is therefore displayed side-by-side from the correct projection direction. However, the size and position of the depicted CT data set frequently do not coincide with the x-ray image.

Instead of the two known approaches, now a registered side-by-side presentation is sought so that both the projection direction and the size and table position are included in said side-by-side presentation. This has the advantage that all possible movements of the angiography system (including table and zoom) are adapted in the depiction of the CT. The system can therefore be positioned without radiation if the ideal projection direction for a defined vessel segment is additionally indicated to the interventionalist via color coding. This is important primarily given long-duration procedures with frequently necessary changing of the table position and C-arm position. This provides the advantage of a radiation-free positioning capability of the C-arm, and the more intuitive side-by-side guidance, because with the registered side-by-side presentation the size of the vascular tree always coincides with the x-ray image.

The invention can be briefly summarized as follows: method for graphical assistance in an interventional procedure to open an occlusion of a hollow organ of a patient, with the following steps:

1. retrieve a three-dimensional CT image data set of an examination region with the at least one hollow organ having the occlusion; determine or retrieve segmentation data of the CT image data set; and visualize the three-dimensional CT image data set with the (in particular shown) segmentation data of the hollow organ at a display unit, 2. acquire at least two x-ray images by means of a fluoroscopy image acquisition system given different angulations and registration of the CT image data set with regard to at least two of the x-ray images, 3. continuously acquire a plurality of x-ray images with the fluoroscopy image acquisition system during a determinable time period, and joint real-time visualization of at least one respective x-ray image and data of the CT image data set at the display unit, and 4. store information of the method after the end of the acquisition, wherein the steps are implemented individually and in sequence, and control options relating exclusively to the current step can be selected manually by means of a user interface depending on the step which is implemented, and only corresponding user inputs are accepted that are appropriate for the current step.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for computerized graphical assistance in an interventional medical procedure to open an occlusion of a hollow organ of a patient, comprising:
   (1) providing a computerized processor with a three-dimensional computed tomography (CT) image data set of an examination region of a patient comprising at least one hollow organ having an occlusion, determining or retrieving segmentation data of the CT image data set designating the hollow organ, and displaying the three-dimensional CT image data set with the segmentation data of the hollow organ at a display unit, as a displayed image;
   (2) operating an x-ray fluoroscopy image acquisition system to acquire at least two fluoroscopy images at different angles with respect to said hollow organ, and, in said processor, bringing the CT image data set into registration with at least two of said x-ray fluoroscopy images;
   (3) operating the x-ray fluoroscopy system to continually acquire a plurality of additional x-ray fluoroscopy images during a predetermined time period, and providing a real time visualization, at said display unit, of at least one of said additional fluoroscopy images and said displayed image data set;
   (4) storing at least the images displayed in step (3); and
   (5) implementing each of steps (1), (2), (3) and (4) individually and in sequence and, at said display unit, presenting control options relating exclusively to each individual step and allowing said control options to be manually selected via a user interface in communication with said processor depending on the individual step being implemented, and, while each step is being individually implemented, accepting user inputs into said processor via said user interface only for the step that is currently being individually implemented.

2. A method as claimed in claim 1 comprising implementing steps (1), (2), (3) and (4) automatically in said processor.

3. A method as claimed in claim 1 comprising:
   (1a) between (1) and (2), determining, in said processor, at least one parameter describing an attribute of said occlusion from said three-dimensional CT image data set.

4. A method as claimed in claim 1 comprising in (1a) between (1) and (2), determining at least one of a centerline of said hollow organ or a three-dimensional extent of said hollow organ from said segmentation data, and showing said center line or said three-dimensional extent of said hollow organ in said displayed image in (3).

5. A method as claimed in claim 4 comprising using chronologically most current segmentation data automatically in (1).

6. A method as claimed in claim 4 comprising allowing a presentation of said displayed image to be rotated or otherwise modified in terms of orientation at said display unit.

7. A method as claimed in claim 4 comprising displaying said center line or said three-dimensional extent of said hollow organ highlighted with color or with color coding, at said display unit.

8. A method as claimed in claim 4 comprising, in said processor, generating projection images or MPR images from said CT image data set relative to a selected point at said center line, and displaying said projection images or MPR images.

9. A method as claimed in claim 4 comprising, in said processor, automatically determining a J-CTO score in (1a) as an additional parameter, and displaying said J-CTO score at said display unit.

10. A method as claimed in claim 1 comprising operating said x-ray fluoroscopy imaging acquisition system in (2) with a contrast agent profusion through the hollow organ when acquiring said at least two additional x-ray fluoroscopy images.

11. A method as claimed in claim 1 comprising, in (2), acquiring at least three additional x-ray fluoroscopy images and automatically selecting at least two of said x-ray fluoroscopy images for said registration, or selecting said at least two of said x-ray images for said registration based on a manual input into said processor.

12. A method as claimed in claim 1 comprising, in (2), displaying said x-ray fluoroscopy images with at least one of a center line or a three-dimensional extent of said hollow organ after said registration.

13. A method as claimed in claim 1 comprising, in (3), setting said predetermined time period to correspond to a duration of said interventional medical procedure.

14. A method as claimed in claim 1 comprising displaying the respective images respectively in multiple display windows at said display unit.

15. A method as claimed in claim 1 comprising displaying visualizations of said images at said display unit with color-coding.

16. A method as claimed in claim 1 comprising, in (3), showing said real time visualization with multiple images superimposed or side-by-side.

17. A method as claimed in claim 1 comprising, in (3), displaying said images with a center line of said hollow organ or a three-dimensional lumen of said hollow organ also visualized.

18. A method as claimed in claim 1 comprising allowing said user inputs selected from the group consisting of presentation size, arrangement of images, orientation of images, superimposition of images, number of display windows, and color.

19. A method as claimed in claim 1 comprising, in (4), storing said images according to the DICOM standard.

20. An apparatus for providing computerized graphical assistance in an interventional medical procedure to open an occlusion of a hollow organ of a patient, said apparatus comprising:

a computerized processor having a user interface and a display unit in communication therewith;

an x-ray fluoroscopy image acquisition system;

(1) said computerized processor being configured to receive a three-dimensional computed tomography (CT) image data set of an examination region of a patient comprising at least one hollow organ having an occlusion, determine or retrieve segmentation data of the CT image data set designating the hollow organ, and display the three-dimensional CT image data set with the segmentation data of the hollow organ at the display unit, as a displayed image;

(2) said computerized processor being configured to operate an x-ray fluoroscopy image acquisition system to acquire at least two fluoroscopy images at different angles with respect to said hollow organ, and to bring the CT image data set into registration with at least two of said x-ray fluoroscopy images;

(3) said computerized processor being configured to operate the x-ray fluoroscopy system to continually acquire a plurality of additional x-ray fluoroscopy images during a predetermined time period, and to provide a real time visualization, at said display unit, of at least one of said additional fluoroscopy images and said displayed image data set;

(4) said computerized processor being configured to store at least the images displayed in step (3); and (5) said computerized processor being configured to implement each of steps (1), (2), (3) and (4) individually and in sequence and, at said display unit, present control options relating exclusively to each individual step and allow said control options to be manually selected via the user interface depending on the individual step being implemented, and, while each step is being individually implemented, accept user inputs into said processor via said user interface only for the step that is currently being individually implemented.

* * * * *